United States Patent [19]

Walker

[11] 4,259,959
[45] Apr. 7, 1981

[54] SUTURING ELEMENT

[76] Inventor: Wesley W. Walker, 1253 Carrell La., Napa, Calif. 94558

[21] Appl. No.: 971,626

[22] Filed: Dec. 20, 1978

[51] Int. Cl.³ .............................................. A61B 17/08
[52] U.S. Cl. ................................................. 128/337
[58] Field of Search .................... 128/334 R, 337, 335

[56] References Cited

U.S. PATENT DOCUMENTS

| 709,392 | 0/1902 | Brown | 128/337 |
|---|---|---|---|
| 2,421,193 | 0/1947 | Gardner | 128/335 |
| 3,134,152 | 0/1964 | Pei | 128/335 |
| 3,214,810 | 0/1965 | Mathison | 128/337 |
| 3,221,746 | 0/1965 | Noble | 128/334 R |
| 3,716,058 | 0/1973 | Tanner, Jr. | 128/337 |
| 3,815,578 | 0/1974 | Bucalo | 128/334 R |
| 3,867,944 | 0/1975 | Samuels | 128/334 R |
| 3,939,828 | 0/1976 | Mohr et al. | 128/334 R |

FOREIGN PATENT DOCUMENTS

| 913464 | of 1949 | Fed. Rep. of Germany | 128/335 |
|---|---|---|---|
| 244558 | of 1969 | U.S.S.R. | 128/337 |

Primary Examiner—Robert W. Michell
Assistant Examiner—C. W. Shedd
Attorney, Agent, or Firm—Townsend and Townsend

[57] ABSTRACT

The disclosed invention is a suturing element comprising a backbone or strip of material with numerous hooks extending therefrom in at least two directions. It is used by inserting it into the wound so that the hooks snag the tissue edges and hold them together while the wound heals.

6 Claims, 5 Drawing Figures

U.S. Patent
Apr. 7, 1981
4,259,959
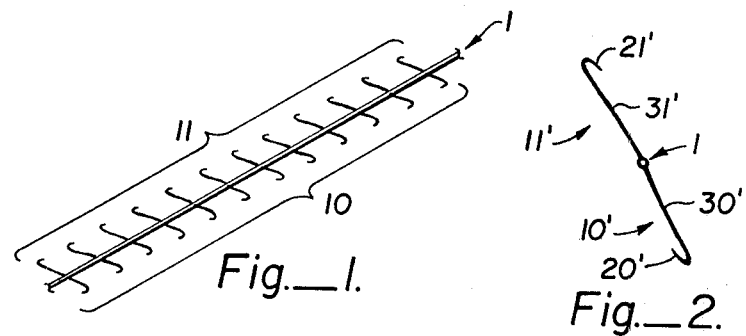
Fig._1.
Fig._2.
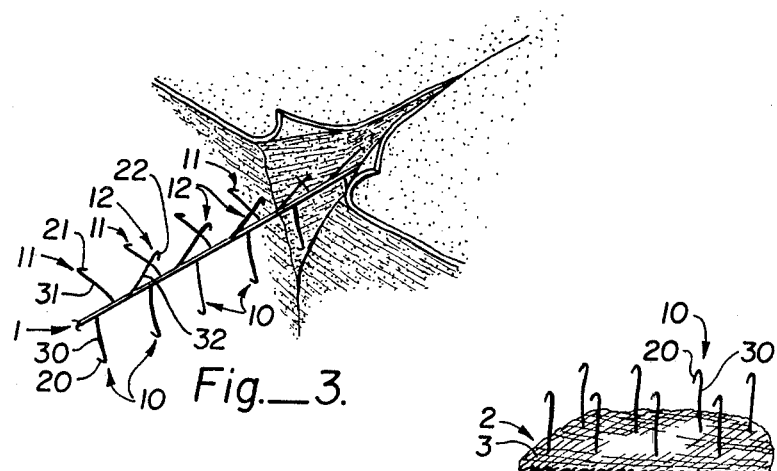
Fig._3.
Fig._4.
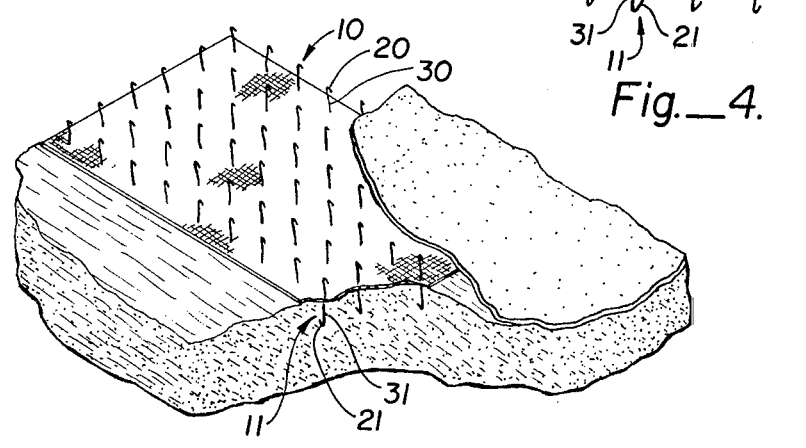
Fig._5.

SUTURING ELEMENT

BACKGROUND OF THE INVENTION

1. Field of the Invention

The present invention relates to a suturing element useful for suturing incisions, lacerations, or the like, and is particularly useful in veterinary medicine.

2. Summary of the Prior Art

In manual suturing of an incision, laceration, or wound, a suture is generally stitched through the tissue and knotted to hold the tissue edges together for healing. In the case of deep wounds or tear wounds where the skin is torn from the fascia, sutures frequently must be stitched through the wound at more than one level, one set of sutures stitching the internal portions of the wound together, another set of sutures stitching the external portions of the wound together. Such suturing operations are very time consuming and especially in the case of tear wounds, can leave pockets where serum, blood, and exudates can collect. Additionally, while suturing the interior portions of the wound, it is difficult to obtain close and even apposition of the tissue edges.

To minimize the difficulties involved in manual suturing, a number of alternate suturing elements have been developed. Several are described in U.S. Pat. Nos. 3,716,058, 816,028, and 2,817,339. Generally, these alternate suturing elements take the form of a shaft with barbs at each end. Some are made of flexible suture material such as "cat gut" and some are formed of more rigid materials. Some can be used in the internal wound area while others can only be used to hold the surface edges together. These alternate suturing elements, however, still present difficulties; each barbed shaft usually replaces only a single stitch of a manual suture and must be individually placed in the wound. As a result, use of these suturing elements is also quite time-consuming, and where suturing is required in internal areas of the wound, close and even apposition of tissue without the development of pockets remains difficult.

SUMMARY OF THE INVENTION

The suturing element of the present invention, however, avoids many problems associated with the use of previous suturing elements. It provides a very quick means for suturing lacerated, incised, or wounded edges together, both in the interior of the wound and near the surface. Simultaneously, it allows close and even apposition of tissue walls without the development of pockets. It is particularly suited for use in veterinary medicine.

Broadly, the present suturing element comprises a backbone or strip of material with numerous hooks extending therefrom in at least two directions. It is used by inserting it into the wound so that the hooks snag the tissue edges and hold them together while the wound heals.

With the selection of a backbone of appropriate length, one suturing element of the present invention can be used where numerous individual stitches or individual barbed sutures would have otherwise been required. Consequently, when a suturing element of the present invention is used, what would have been a time-consuming operation requiring multiple sutures is a simple operation with only one or a few suturing elements. Also, close, even apposition of tissue throughout the wound without the development of undesirable pockets is easily obtained with use of the present invention and tissue irritation due to continued handling of the tissue edges is minimized.

BRIEF DESCRIPTION OF THE DRAWINGS

FIG. 1 is a slightly enlarged perspective view of one embodiment of the present invention which comprises a backbone and two series of hooks extending from the backbone in opposite directions.

FIG. 2 is an enlarged end view of the FIG. 1 embodiment of the present invention particularly illustrating the manner in which the hooks extend from the backbone.

FIG. 3 is an enlarged perspective view of a second embodiment of the present invention with the hooks arranged in a spiral pattern around the backbone and shows this embodiment of the invention partially inserted in a wound.

FIG. 4 is an enlarged perspective view of a third embodiment of the invention. In this case, the backbone is in the form of a strip of material with numerous hooks extending from its upper and lower surfaces.

FIG. 5 is a perspective view of the FIG. 4 embodiment of the present invention shown inserted between the fascia and skin in a tear wound to hold the skin and fascia together for healing.

DESCRIPTION OF THE SPECIFIC EMBODIMENTS

Broadly, the present suturing element comprises a backbone or strip of material with numerous hooks extending therefrom. It is inserted into the wound so that the hooks snag the tissue edges and hold them together while the wound heals. The entire suturing element is usually comprised of somewhat flexible material which is non-reactive with living tissue, such as chromic "cat gut" or non-absorbable synthetic materials. Alternately, the suturing element can be made of dissolving suture material; in that case, the suturing element will not remain in the wound after healing.

FIG. 1 illustrates one embodiment of the invention. Two series of hooks, 10 and 11 extend from opposite sides of the backbone 1. The hooks are preferably from about 1/32" to ⅛" in overall length, and the backbone length is variable. As shown in FIG. 2, the hooks, i.e. 11' and 10' are aligned so that the hooking portions 21' and 20' all extend in the same circumferential direction from the hook stems, 31' and 30', shown here as clockwise.

FIG. 3 illustrates another embodiment of the present invention. This embodiment comprises a backbone 1 with three series of hooks, 10, 11, and 12, extending in a spiral pattern from the backbone 1. Again, the hooks are preferably about 1/32" to ⅛" in overall length, and the length of the backbone is variable. The hooks are preferably aligned so that the hooking portions, i.e., 20, 21, and 22, extend in the same circumferential direction from the hook stems 30, 31, and 32, here shown as clockwise.

FIG. 4 illustrates a third embodiment of the invention. In this case the backbone element is essentially in the form of a strip of material 2 having a flat upper surface 3 and a flat lower surface 4. Numerous hooks, 10 and 11, extend from the upper surface and lower surface respectively of the strip of material. In this embodiment of the invention, the hooks are usually arranged in a grip pattern, preferably about ¼" apart, on the strip of material, and preferably are 1/32" to ⅛" in length. Usually, the hooks 10 are aligned so that the hooking portions 20 all extend in the same linear direction from the hook stems 30, and the hooks 11 are also aligned so that all the hooking portions 21 extend in the same linear direction from the hook stems 31. Preferably, the hooking portions 20 extend in one linear direction from the hook stems 30, here to the left, while the hooking portions 21 extend in the opposite linear direction, here to the right, from the hook stems 31.

All embodiments of the invention can be conveniently utilized to hold together opposing tissue walls in a laceration or incision. However, the FIG. 1 embodiment is particularly suited to applications wherein two opposed tissue walls are to be sutured. The FIG. 3 embodiment can be utilized particularly conveniently in tear wounds where the tissue walls have irregular faces, so the three hooks can snag and evenly oppose the tissue of the wound. For example, in FIG. 3, the invention is shown partially inserted into a wound where one set of hooks 12 snags the skin while the other two sets of hooks snag the two side walls of the wound.

The FIG. 4 embodiment of the invention can also be utilized in many applications but is particularly suited for large tear wounds where the skin is torn from the fascia. This is illustrated in FIG. 5 where the FIG. 4 embodiment has been placed in such a tear wound so that the hooks 10 on the upper surface snag the skin while the hooks 11 on the lower surface snag the underlying fascia.

Normally, in order to use the present invention, one first examines the wound or incision to determine the type and length of appropriate suturing element. After an appropriate suturing element of the desired length has been selected, it is then carefully placed in the wound. Usually slight pressure is then applied to the surrounding tissue to cause the hooks to snag the tissue and hold it together while the wound heals. The wound is then allowed to heal with the suturing element in place. Because one suturing element of the present invention replaces numerous individual sutures, the time involved in suturing the wound, particularly if it is a large tear wound, is minimized. Furthermore, close apposition of the tissue without the development of pockets is easily obtained.

Naturally, it will be understood that the above description and drawings are intended by way of illustration and not by way of limitation and that numerous variations and modifications are within the scope of the invention, which is defined by the appended claims.

What is claimed is:

1. A suturing element comprising:
 a backbone where said backbone is a relatively thin strip of material having flat upper and lower surfaces;
 a first set of hooks extending substantially perpendicularly from the upper surface in a first direction;
 a second set of hooks extending from the lower surface in a second direction, said first and second directions being opposite to each other;
 each of said hooks having a stem and means for snagging tissue;
 said snagging means of said first set of hooks being aligned in a third direction and said snagging means of said second set of hooks being aligned in a fourth direction; and
 substantially all of said directed snagging means on a given side of said thin strip lie in a plane which is substantially parallel to the adjacent surface of said thin strip.

2. The suturing element of claim 1 wherein said hooks are arranged on said upper and lower surface in about a ¼" grid pattern spacing.

3. The suturing element of claim 2 wherein said hooks are approximately 1/32" to ⅛" in length.

4. The suturing elements of claim 1 wherein said backbone is made of somewhat flexible material and said suturing material is made of biologically compatible material.

5. The suturing element of claim 1 wherein said third and fourth directions are opposite directions.

6. A suturing system for an open wound having opposing tissue surfaces comprising:
 a backbone, said backbone being a relatively thin strand;
 three sets of hooks, said sets of hooks extending from said backbone in different radial directions;
 said hooks having a stem and means for snagging tissue, said snagging means extending in the same circumferential direction with respect to said backbone and lying in parallel planes;
 said directions of said sets being sufficiently divergent so that when said suturing element is placed within a wound, said snagging means snag the opposing tissue surfaces of said wound as said tissue surfaces are forced together.

* * * * *